United States Patent [19]
Chick et al.

[11] Patent Number: 6,040,194
[45] Date of Patent: *Mar. 21, 2000

[54] METHODS AND DEVICE FOR DETECTING AND QUANTIFYING SUBSTANCES IN BODY FLUIDS

[75] Inventors: William L. Chick, Wellesley; David E. Wolf, Hudson, both of Mass.; Richard A. Cardullo, Riverside, Calif.

[73] Assignee: Sensor Technologies, Inc., Shrewsbury, Mass.

[ * ] Notice: This patent is subject to a terminal disclaimer.

[21] Appl. No.: 08/467,915

[22] Filed: Jun. 6, 1995

Related U.S. Application Data

[63] Continuation of application No. 08/302,396, Sep. 8, 1994, abandoned, which is a continuation of application No. 08/160,444, Dec. 1, 1993, abandoned, which is a continuation of application No. 07/905,729, Jun. 29, 1992, abandoned, which is a continuation-in-part of application No. 07/452,122, Dec. 14, 1989, Pat. No. 5,342,789.

[51] Int. Cl.$^7$ .............................. A61B 5/00; A61B 8/00; G01N 21/64; A61K 49/00
[52] U.S. Cl. ...................... 436/501; 128/634; 422/82.07; 422/82.08; 424/9.1; 424/9.6; 435/4; 435/7.4; 435/7.7; 435/7.9; 435/7.92; 435/7.72; 436/95; 436/537; 436/805; 436/807; 436/815
[58] Field of Search .............................. 436/95, 501, 537, 436/805, 807, 815; 604/632, 633; 424/9.1, 9.6; 128/634; 435/4, 7.4, 7.7, 7.9, 7.92, 7.72, 6; 422/82.07, 82.08

[56] References Cited

U.S. PATENT DOCUMENTS

| | | | |
|---|---|---|---|
| 4,041,932 | 8/1977 | Fostick | 128/2 G |
| 4,071,020 | 1/1978 | Pugliese . | |
| 4,330,299 | 5/1982 | Cerami | 435/11 X |
| 4,344,438 | 8/1982 | Schultz . | |
| 4,401,122 | 8/1983 | Clark, Jr. | 435/11 X |
| 4,981,779 | 1/1991 | Wagner . | |
| 5,001,051 | 3/1991 | Miller et al. | 435/6 |
| 5,028,787 | 7/1991 | Rosenthal et al. . | |
| 5,101,814 | 4/1992 | Palti | 128/635 |
| 5,143,066 | 9/1992 | Komives et al. | 128/634 |
| 5,244,636 | 9/1993 | Walt et al. | 422/82.07 |
| 5,320,814 | 6/1994 | Walt et al. | 422/82.07 |
| 5,326,531 | 7/1994 | Hahn et al. | 422/82.06 |
| 5,341,805 | 8/1994 | Stavridi et al. | 128/635 |
| 5,342,789 | 8/1994 | Chick et al. | 436/501 |
| 5,460,971 | 10/1995 | Gottlieb | 436/68 |

FOREIGN PATENT DOCUMENTS

WO 9010861  9/1990  WIPO .

OTHER PUBLICATIONS

Kirk–Othmer Encyclopedia of Chemical Technology, fourth edition, John Wiley & Sons publishers, New York, vol. 4, pp. 208–220, "Biosensors", 1992.

R. Cardullo et al., *Proc. Nat'l Acad. Sci USA*, vol. 25, pp. 8790–8794, Dec. 1988.

M. Heller et al in Rapid Detection and Identification of Infectious Agents, Printed by Academic Press, Inc. 1985, pp. 245–256.

D. Meadows et al, *TALANTA*, vol. 35, No. 2, pp. 145–150, 1988.

Meadows et al., "Fiber–Optic Biosensors Based on Fluorescence Energy Transfer", *Talanta*, vol. 35, No. 2, pp. 145–150, 1988.

Heller, et al., "Chemiluminscent and Fluorosecnt Probes for DNA Hybridization Systems", *Rapid Detection and Identification of Infectious Agents*, pp. 245–257, 1985.

Cardullo, et al., "Detection of Nucleic Acid Hybridization by Nonradiative Fluorescence Resonance Energy Transfer", *Proc. Nat. Ac. Sci. U.S.A.* (85), 1988.

*Primary Examiner*—James C. Housel
*Assistant Examiner*—Ja-Na Hines
*Attorney, Agent, or Firm*—Fish & Richardson, P.C., P.A.

[57] ABSTRACT

An in vivo method and apparatus for detecting an analyte in an individual. A sensor that includes a fluorescence reagent is placed in communication with the body fluids of the individual suspected of containing the analyte in such a way that once in place said sensor does not exit the skin of the individual. The sensor is configured to retain the fluorescence reagent while allowing analyte to diffuse into and out of said sensor. The sensor is illuminated transdermally, and the fluorescence from the fluorescence reagent associated with the presence of the analyte is measured.

30 Claims, 13 Drawing Sheets

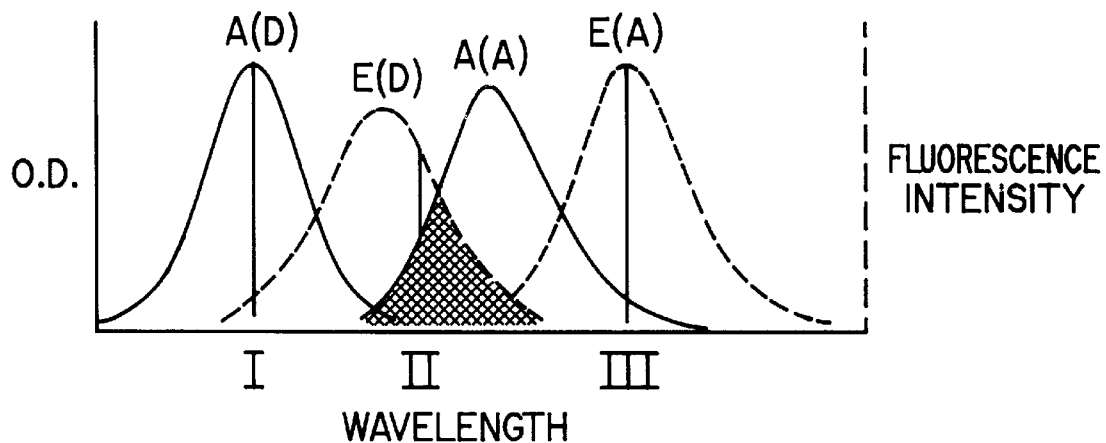
FIG. 1a
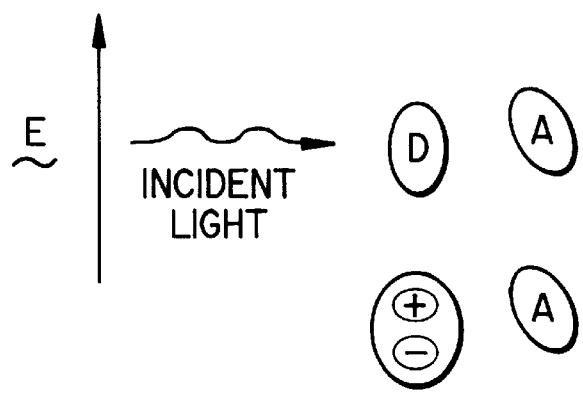
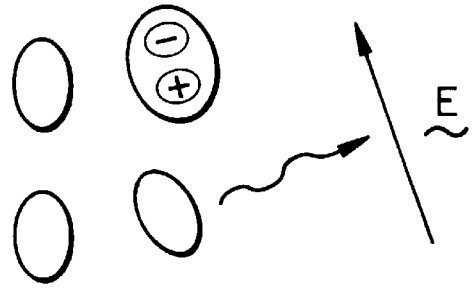
FIG. 1b

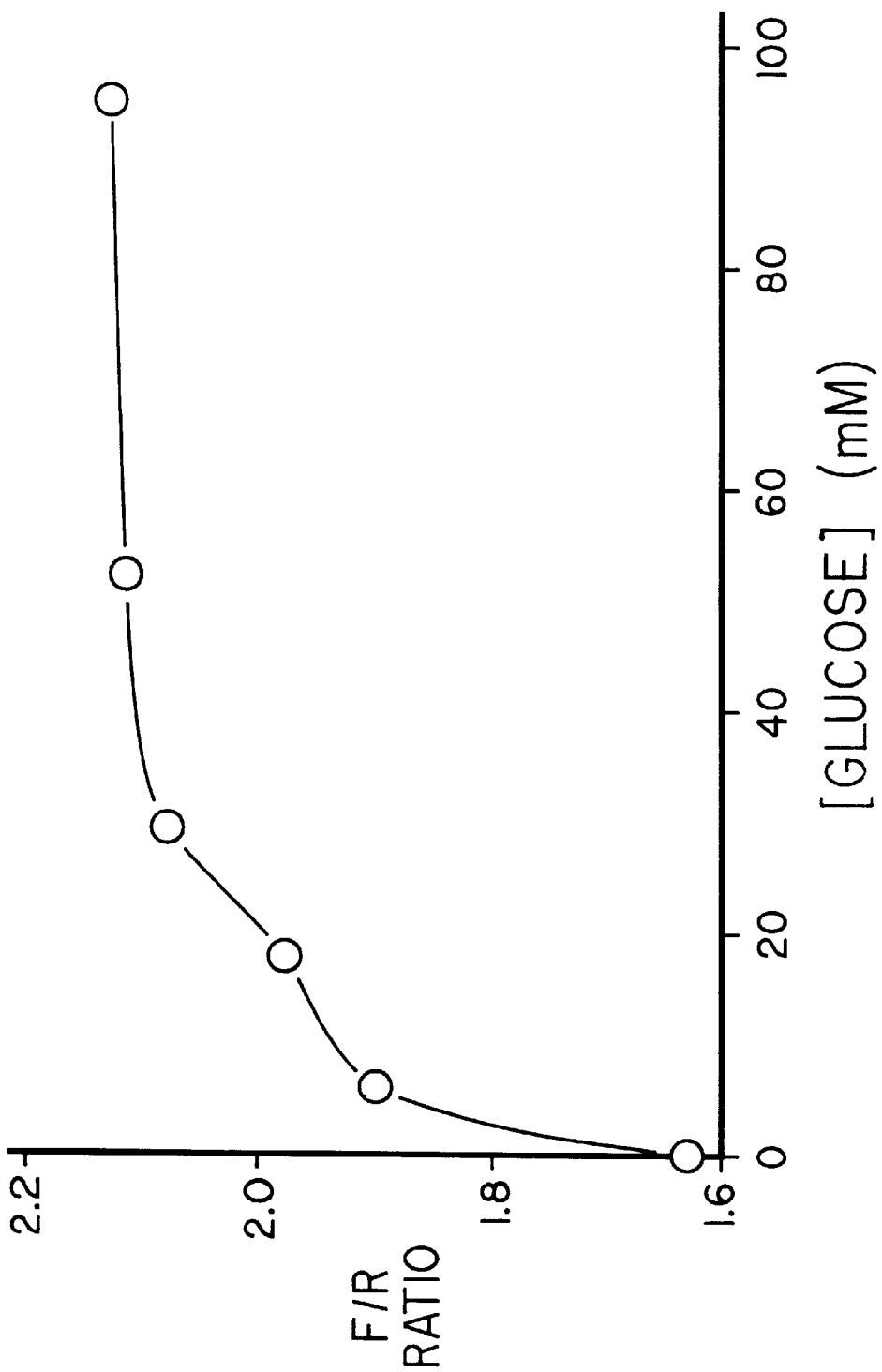

METHODS AND DEVICE FOR DETECTING AND QUANTIFYING SUBSTANCES IN BODY FLUIDS

CROSS REFERENCE TO RELATED APPLICATIONS

This application is a continuation of U.S. Ser. No. 08/302, 396 filed Sep. 8,1994, now abandoned which is a continuation of Chick et al., U.S. Ser. No. 08/160,444 filed Dec. 1, 1993 entitled "Method and Device for Detecting and Quantifying Substances in Body Fluids," now abandoned, which is a continuation of Chick et al., U.S. Ser. No. 07/905,729 filed Jun. 29, 1992 entitled "Method and Device for Detecting and Quantifying Substances in Body Fluids," now abandoned, which is a continuation in part of Chick et al., U.S. Ser. No. 07/452,122 filed Dec. 14, 1989 entitled "Method and Device for Detecting and Quantifying Glucose in Body Fluids," now U.S. Pat. No. 5,342,789, which is assigned to the same assignee as the present application and is hereby incorporated by reference in its entirety.

BACKGROUND OF THE INVENTION

This application relates to detecting and quantifying substances in body fluids using fluorescence techniques.

Various methods for detecting and quantifying substances in body fluids are known. For example, in the case of glucose these methods include various colorimetric reactions, measuring a spectrophotometric change in the property of any number of products in a glycolytic cascade or measuring the oxidation of glucose using a polarographic glucose sensor.

U.S. Pat. No. 4,401,122 discloses an in vivo method for measuring substances such as glucose which involves placing an enzyme (e.g., glucose oxidase) either in or under the skin and detecting the enzymatic reaction product (e.g., oxygen) directly through the skin either colorimetrically or by using polarographic or enzyme electrodes. The amount of enzymatic reaction product detected is a measure of the amount of substrate.

Cerami, U.S. Pat. No. 4,330,299 describes an assay for measuring glucose concentration in which detection is carried out by means of color-producing agents or reagents which form precipitates. In one embodiment, for example, rhodamine is bonded to a lectin and a carbohydrate is affixed to a solid support. The rhodamine-labelled lectin reversibly binds to the carbohydrate in the absence of glucose. When glucose is introduced, it binds to the lectin, thereby displacing the rhodamine-labelled lectin from the carbohydrate. The complexed and uncomplexed rhodamine-lectin are then physically separated, and the reduction in color intensity displayed by rhodamine-lectin bound to carbohydrate is measured as an indication of glucose concentration.

Although such conventional assays have proven reliable, the reagents on which they rely become exhausted or must be removed. Therefore, these assays require the use of disposable sticks or replaceable cartridges, which can be expensive and inconvenient for the active user.

Meadows and Schultz describe another method by which blood glucose levels can be determined using optical means. They describe a fiber optic glucose sensor based on the competitive binding of glucose and fluorescein-labelled dextran (FITC-dextran) to rhodamine-labelled concanavalin A (Rh-Con A), Meadows, D. and J. S. Schultz, *Talanta*, 35:145–150 (1988).

The Meadows and Schultz optical sensor is attended by many problems, which means it is of limited use in a clinical setting or in monitoring blood glucose levels in individuals on a day to day basis. First, as mentioned in the article, the sensor can only detect glucose concentrations up to 2.00 mgs/ml. Although the normal blood glucose concentration in man is approximately 1.00 mg/ml., the concentration of glucose in diabetic blood can often exceed 3.00–4.00 mg/ml., which is well beyond the upper limit of the sensor described.

Second, Meadow's and Schultz's sensor has a short life because, as mentioned in the article, the dextran aggregates and becomes precipitated. Third, only 45% of the fluorescence is quenched using the Meadows and Schultz optical sensor. This effect may not be dramatic enough to be detected.

Finally, the in vivo use of a fiber optic is clinically impractical because in order to work, it must pierce the skin. Therefore, it requires an invasive technique and puts the patient at significant risk for developing serious infection. This is particularly true in diabetic patients who are known to have reduced resistance to infection.

An ideal sensor should be capable of detecting a wide range of physiological concentrations of analyte. As used herein, "physiological concentration" refers to the concentration of analyte found in both normal and pathological states. For example, in the case of glucose it refers to glucose levels found in normal, hypoglycemic, and hyperglycemic patients.

The sensor should also be reliable, reusable and easy to use. In addition, the in vivo sensor should be non-invasive.

SUMMARY OF THE INVENTION

In a first aspect, the invention features an in vivo method and sensor for detecting an analyte in an individual (as used herein, "detecting" may include qualitatively determining the presence of an analyte, as well as quantitatively measuring its concentration). The sensor is placed in communication with the body fluids (e.g., blood, plasma, or serum) the individual suspected of containing the analyte in such a way that once in place the sensor does not exit the skin of the individual. We refer to such placement as permitting non-invasive detection and monitoring of the analyte. The sensor includes a fluorescence reagent for detecting the analyte and is configured to retain the fluorescence reagent while allowing analyte to diffuse into and out of the sensor. In this way, the sensor can be used for extended monitoring because depletion of the fluorescence reagent is minimized, if not eliminated. Once the sensor is in place, it is illuminated with radiation transdermally and the fluorescence from the fluorescence reagent associated with the presence of the analyte is measured.

As used herein, "fluorescence" refers to radiation emitted in response to excitation by radiation of a particular wavelength. It includes both short-lived (nanosecond range) and long-lived excited state lifetimes; the latter is sometimes referred to as phosphorescence.

As used herein, "fluorescence reagent" refers to a material whose fluorescence behavior (e.g., intensity, emission spectrum, or excitation spectrum) changes in the presence of the analyte being detected.

In some embodiments, it binds reversibly to the analyte. For example, the reagent may be a fluorophore (or compound labelled with such a molecule) that binds directly to the analyte. It is the fluorescence behavior of this molecule (or compound labelled with this molecule) which changes as a result of analyte binding.

The reagent may also include more than one component. For example, it may include an analogue to the analyte labelled with a fluorophore and a ligand (e.g., an antibody, receptor for the analyte, lectin, enzyme, or lipoprotein) that binds competitively (and specifically) to the analogue and the analyte. In this case, it is the fluorescence behavior of the labelled analogue which changes as a result of ligand binding to analyte. Conversely, ligand may be labelled, rather than the analogue, in which case it is the fluorescence behavior of the labelled ligand which changes.

The reagent may also include two components, one of which is labelled with an energy-absorbing donor molecule and the other of which is labelled with an energy-absorbing acceptor molecule; the donor and acceptor have overlapping excited state energy levels. One or both molecules forming the donor-acceptor pair can be fluorophores. Regardless, however, it is the fluorescence associated with the non-radiative resonance energy transfer from donor to acceptor that is measured. This transfer is often referred to as "FRET" (an acronym for non-radiative fluorescence resonance energy transfer). The components may be members of a specific binding pair (e.g., an analogue of the analyte and a ligand capable of binding competitively (and specifically) to both the analogue and the analyte) or ligands (e.g., antibodies or oligonucleotides) that bind specifically to different portions of the analyte.

FRET can also be measured where a single reagent capable of binding to the analyte is labelled with both donor and acceptor molecules.

As used herein, "fluorophore" refers to a molecule that absorbs energy and then emits light.

As used herein, "analogue" refers to a material that has at least some binding properties in common with those of the analyte such that there are ligands that bind to both. The analogue and the analyte, however, do not bind to each other. The analogue may be a derivative of the analyte such as a compound prepared by introducing functional chemical groups onto the analyte which do not affect at least some of the binding properties of the analyte. Another example of a derivative is a lower molecular weight version of the analyte which nonetheless retains at least some of the binding properties of the analyte.

In other embodiments, the fluorescence reagent does not bind to the analyte except transiently. In other words, binding to analyte in and of itself is not the cause of the detectable fluorescence change. Instead, in these embodiments detection involves an irreversible chemical reaction, with an accompanying change in fluorescence; the chemical reaction may be proceeded by binding to analyte.

In one example, the fluorescence reagent may include an enzyme and a co-factor or substrate that reacts with the analyte in the presence of the enzyme with an accompanying fluorescence change. In the case where the enzyme reacts with substrate, a co-factor may also be present to assist the reaction.

In another example, the analyte is an enzyme and the fluorescence reagent includes a substrate that is altered (e.g., cleaved) by the enzyme with an accompanying fluorescence change. In yet another example, the fluorescence reagent includes (a) an enzyme in whose presence the analyte reacts to form a detectable product and (b) an indicator for detecting the presence of the product.

In another example, the fluorescence reagent includes (a) a substrate or co-factor capable of reacting with an enzyme to cause a detectable fluorescence change, (b) a first ligand labelled with a first portion of that enzyme and capable of binding to a first portion of the analyte, and (c) a second ligand labelled with a second (different) portion of the enzyme and capable of binding to a second (different) portion of the analyte. Neither the first portion nor the second portion of the enzyme is capable individually of interacting with the substrate or co-factor to produce a detectable fluorescence change. However, binding of the first and second ligands to the analyte causes the first and second enzyme portions to interact with each other, thereby reconstituting the enzyme. The reconstituted enzyme can then react with the substrate or co-factor, with a concomitant change in fluorescence.

A variation of this approach involves an analogue of the analyte labelled with a first portion of the enzyme and a ligand labelled with a second portion of the enzyme. In the absence of analyte, the analogue and analyte bind to each other, thereby reconstituting the enzyme and allowing reaction with substrate or co-factor, with accompanying fluorescence. The presence of analyte disrupts analogue-ligand binding, and thus reconstitution of the enzyme, with an accompanying decrease in fluorescence (since the individual enzyme portions cannot interact with the substrate or co-factor to cause a detectable fluorescence change).

Regardless of whether the fluorescence reagent binds to analyte, changes in fluorescence associated with the presence of the analyte may be measured in several ways. These changes include changes in the excited state lifetime of, or fluorescence intensity emitted by, the fluorophore (or compound labelled with the fluorophore). They also include changes in the excitation or emission spectrum of the fluorophore (or compound labelled with the fluorophore). Changes in the excitation or emission spectrum, in turn, may be measured by measuring (a) the appearance or disappearance of emission peaks, (b) the ratio of the signal observed at two or more emission wavelengths, (c) the appearance or disappearance of excitation peaks, or (d) the ratio of the signal observed at two or more excitation wavelengths.

In the case of FRET, the illumination wavelength may be selected such that it predominantly excites only the donor molecule. We say "predominantly" because due to bleed-through phenomena, it is possible that there will be some acceptor excitation as well. Thus, as used herein, "excitation" of donor or acceptor will refer to an excitation wavelength that predominantly excites donor or acceptor.

Following excitation, non-radiative fluorescence resonance energy transfer is determined by measuring the ratio of the fluorescence signal at two emission wavelengths, one of which is due to donor emission and the other of which is due to acceptor emission. Just as in the case of excitation, there may be some "bleeding" of the fluorescence signal such that acceptor emission makes a minor contribution to the donor emission signal, and vice versa. Thus, whenever we refer to a signal as being "due to" donor emission or acceptor emission, we mean that the signal is predominantly due to donor emission or acceptor emission.

Alternatively, the illumination may be selected such that it excites the donor at a first wavelength and the acceptor at a second wavelength. In other words, two separate excitation events, each at a different wavelength, are used. In this case, non-radiative fluorescence energy transfer is determined by measuring the ratio of the fluorescence signal due to the acceptor following donor excitation and the fluorescence signal due to the acceptor following acceptor excitation.

FRET can also be measured by assessing whether there is a decrease in donor lifetime, a quenching of donor fluorescence intensity, or an enhancement of acceptor fluorescence intensity; the latter two are measured at a wavelength in response to excitation at a different wavelength (as opposed to the ratio measurements described above, which involve either measuring the ratio of emissions at two separate wavelengths or measuring the ratio of emission at a wavelength due to excitation at two separate wavelengths).

A large number of analytes may be detected according to the method of the invention. Suitable analytes include, for example, carbohydrates (e.g., glucose, fructose, and derivatives thereof). As used herein, "carbohydrate" refers to any of the group of organic compounds composed of carbon, hydrogen, and oxygen, including sugars, starches, and celluloses. Other suitable analytes include glycoproteins (e.g., glycohemoglobin, thyroglobulin, glycosylated albumin, and glycosylated apolipoprotein), glycopeptides, and glycolipids (e.g., sphingomyelin and the ganglioside $G_{M2}$).

Another group of suitable analytes includes ions. These ions may be inorganic or organic. Examples include calcium, sodium, chlorine, magnesium, potassium, bicarbonate, phosphate, and carbonate. The invention is also useful for detecting proteins and peptides (the latter being lower molecular weight versions of the former); a number of physiological states are known to alter the level of expression of proteins in blood and other body fluids. Included within this group are enzymes (e.g., enzymes associated with cellular death such as LDH, SGOT, SGPT, and acid and alkaline phosphatases), hormones (e.g., hormones associated with ovulation such as luteinizing hormone and follicle stimulating hormone, or hormones associated with pregnancy such as human chorionic gonadotropin), lipoproteins (e.g., high density, low density, and very low density lipoprotein), and antibodies (e.g., antibodies to diseases such as AIDS, myasthenia gravis, and lupus). Antigens and haptens are also suitable analytes.

Additionally, the invention is useful for detecting and monitoring analytes such as steroids (e.g., cholesterol, estrogen, and derivatives thereof). In the case of estrogen, the invention makes it possible to monitor menopausal patients under estrogen therapy (where estrogen levels can be quite high). The invention is also useful for detecting and monitoring substances such as theophylline (in asthma patients) and creatinine (a substance associated with renal failure).

The invention may also be used to detect and monitor pesticides and drugs. As used herein, "drug" refers to a material which, when ingested, inhaled, absorbed, or otherwise incorporated into the body produces a physiological response. Included within this group are alcohol, therapeutic drugs (e.g., chemotherapeutic agents such as cyclophosphamide, doxorubicin, vincristine, etoposide, cisplatin, and carboplatin), narcotics (e.g., cocaine and heroin), and psychoactive drugs (e.g., LSD).

The invention may also be used to detect and monitor polynucleotides (e.g., DNA and RNA). For example, overall DNA levels may be assayed as a measure of cell lysis. Alternatively, the invention could be used to assay for expression of specific sequences (e.g., HIV RNA).

To permit in vivo operation, the sensor may be provided with a selectively permeable membrane that permits analyte (but not fluorescence reagent) to diffuse into and out of the sensor. In another embodiment, at least some of the components of the fluorescence reagent are immobilized within the sensor (e.g., on a substrate or within the pores of a porous matrix). For example, in the case of an analogue labelled with donor and a ligand labelled with acceptor, one (or both) materials can be immobilized. In another embodiment, at least some of the components of the fluorescence reagent are freely mobile (i.e., not immobilized) within the sensor.

A drug delivery system in communication with the sensor (e.g., via a biofeedback loop) may also be implanted in the individual. The drug delivery system is configured to release a prescribed amount of a drug in response to the level of analyte detected by said sensor.

In a second aspect, the invention features an in vivo method for detecting an analyte in an individual that is not limited to non-invasive monitoring. According to this method, the sensor (containing a fluorescence reagent for detecting the analyte that reversibly binds to the analyte is placed in communication with the body fluids of the individual suspected of containing the analyte. The sensor is configured to retain the fluorescence reagent while allowing analyte to diffuse into and out of said sensor. The fluorescence reagent includes a specific binding pair, one member of which is labelled with an energy-absorbing donor molecule (which may be a fluorophore) and the other of which is labelled with an energy-absorbing acceptor molecule (which may be a fluorophore). The excited state energy level of the donor overlaps with the excited state energy level of the acceptor. The sensor is illuminated so as to i) excite the donor or ii) excite both the donor and acceptor. The fluorescence from the fluorescence reagent associated with the presence of the analyte is then measured by determining the extent to which non-radiative fluorescence resonance energy transfer ("FRET") occurs between the donor and the acceptor upon binding. The non-radiative fluorescence resonance energy transfer, in turn, is determined by measuring i) the ratio of the fluorescence signal at two emission wavelengths, one of which is due to donor emission and the other of which is due to acceptor emission, when only the donor is excited, or ii) the ratio of the fluorescence signal due to the acceptor following donor excitation and the fluorescence signal due to the acceptor following acceptor excitation.

The method and devices of the present invention can be used to detect a wide range of physiological analyte concentrations (e.g., concentrations ranging from 0.5 to 18 mg/ml in the case of glucose). In addition, the method is reliable. Also, because the reactants are not consumed, the devices are reusable for extended periods. Moreover, many of the in vivo embodiments are non-invasive.

Other features and advantages of the invention will be apparent from the following description of the preferred embodiments thereof, and from the claims.

BRIEF DESCRIPTION OF THE DRAWINGS

FIG. 1A is a graphic representation of absorbance and emission spectra of donor and acceptor molecules.

FIG. 1B is a representation of non-radiative energy transfer.

horse serum; (+10) normal horse serum +10 mM glucose; (HS) normal horse serum; (0) Hanks Balanced Salt Solution; (+10) normal horse serum +10 mM glucose; (HS) horse serum; (0) Hanks Balanced Salt Solution.

Figure 6A:
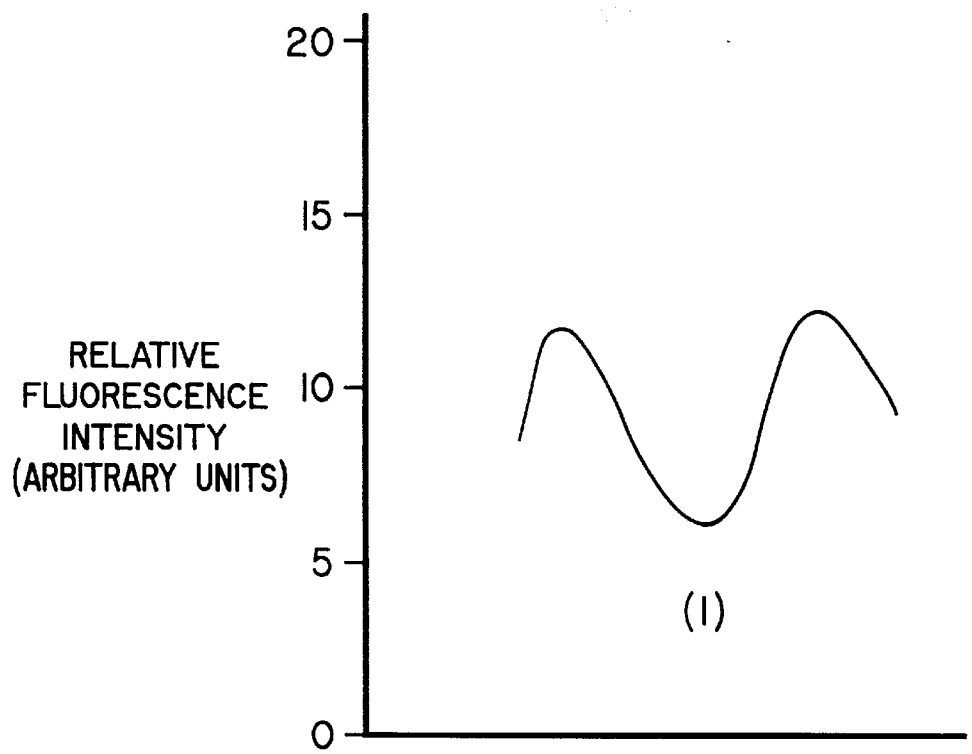

FIG. 6A is a graph representing FRET between FBG and RC with no glucose present (control).

Figure 6B:
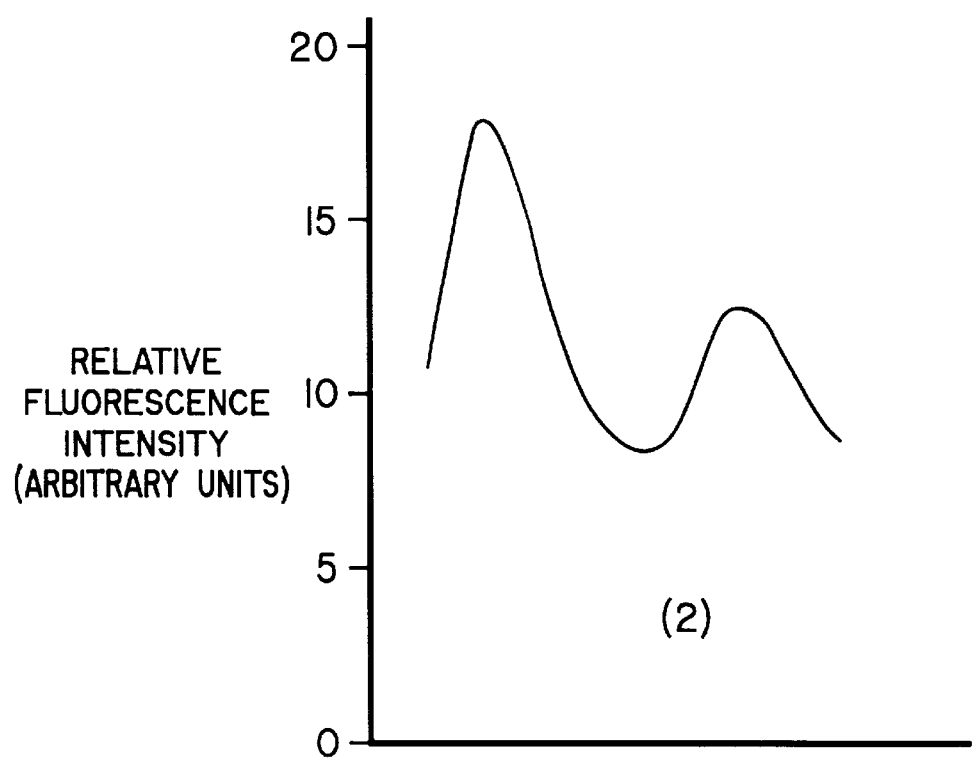

FIG. 6B is a graph representing FRET between FBG and RC microdialyzed against blood containing 3.2 mg/ml. of glucose, similar to what might be found in diabetic patients.

FIG. 7 is a graph representing FRET in response to 150 uls of a mixture of RC and FBG microdialyzed against blood containing varying concentrations of glucose.

Figure 8:
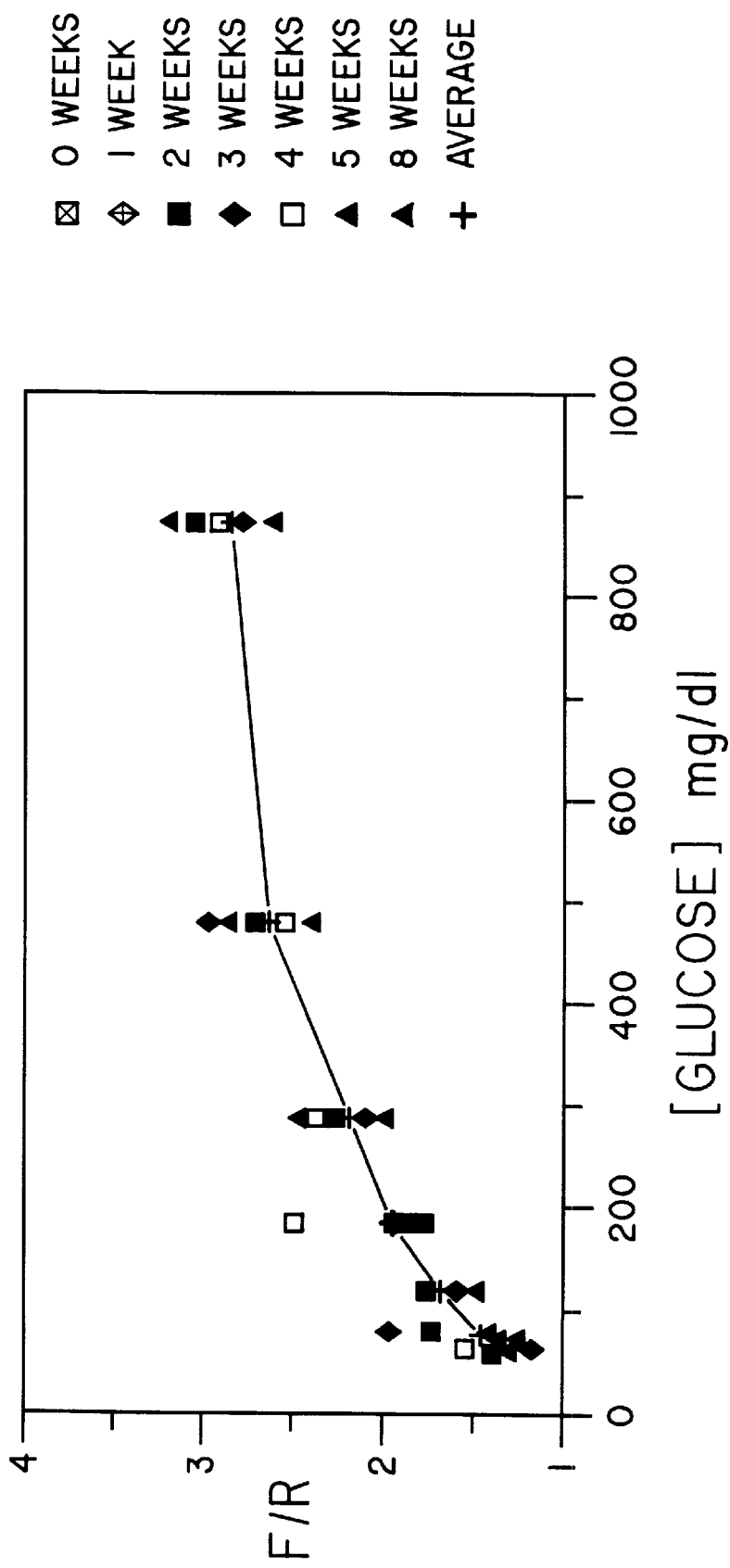

FIG. 8 is a series of titration curves for samples containing various glucose concentrations measured over an eight week period.

Figure 9:
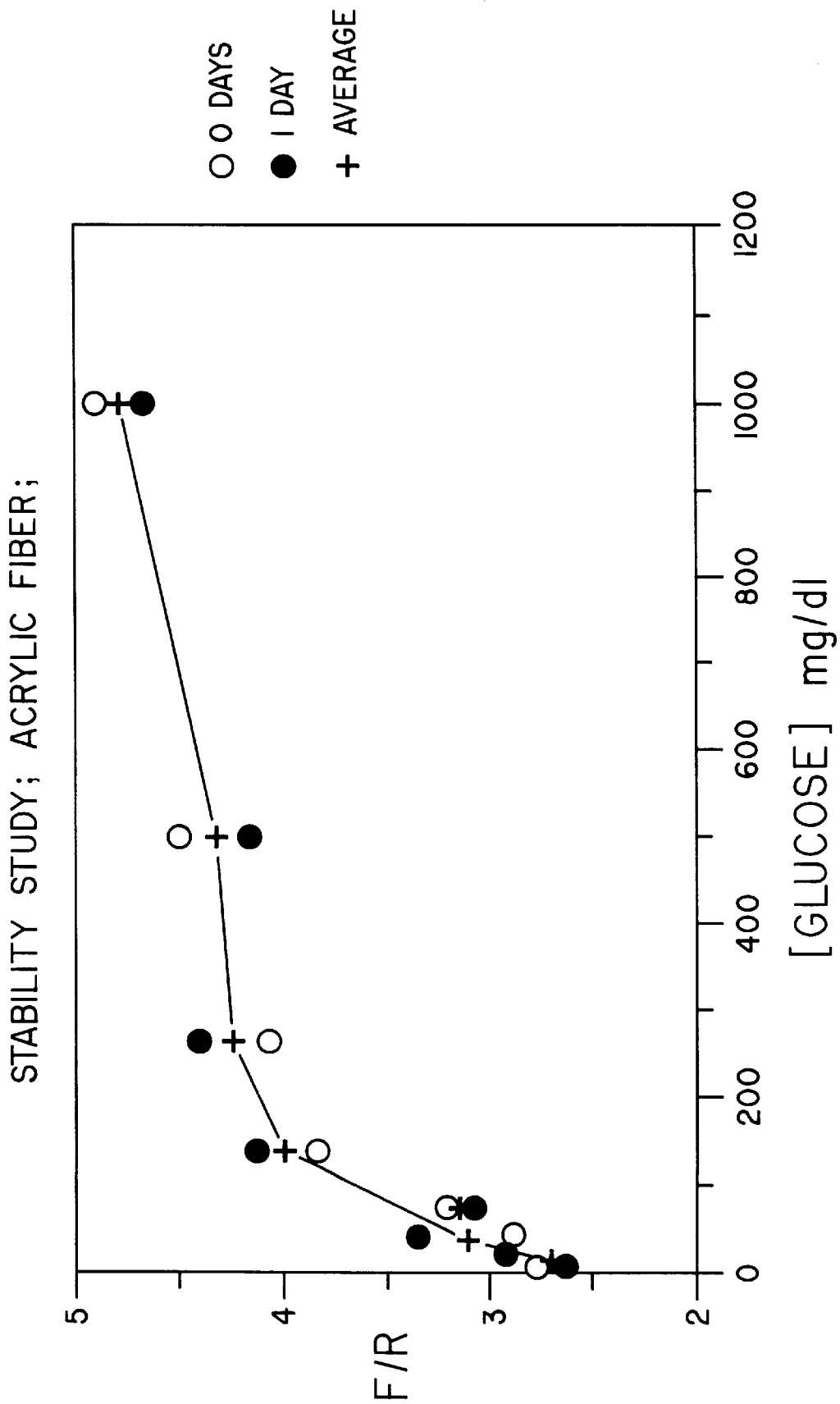

FIG. 9 is a graph representing FRET in response to a mixture of RC and FBG microdialyzed against pooled human serum containing various glucose concentrations.

Figure 10:
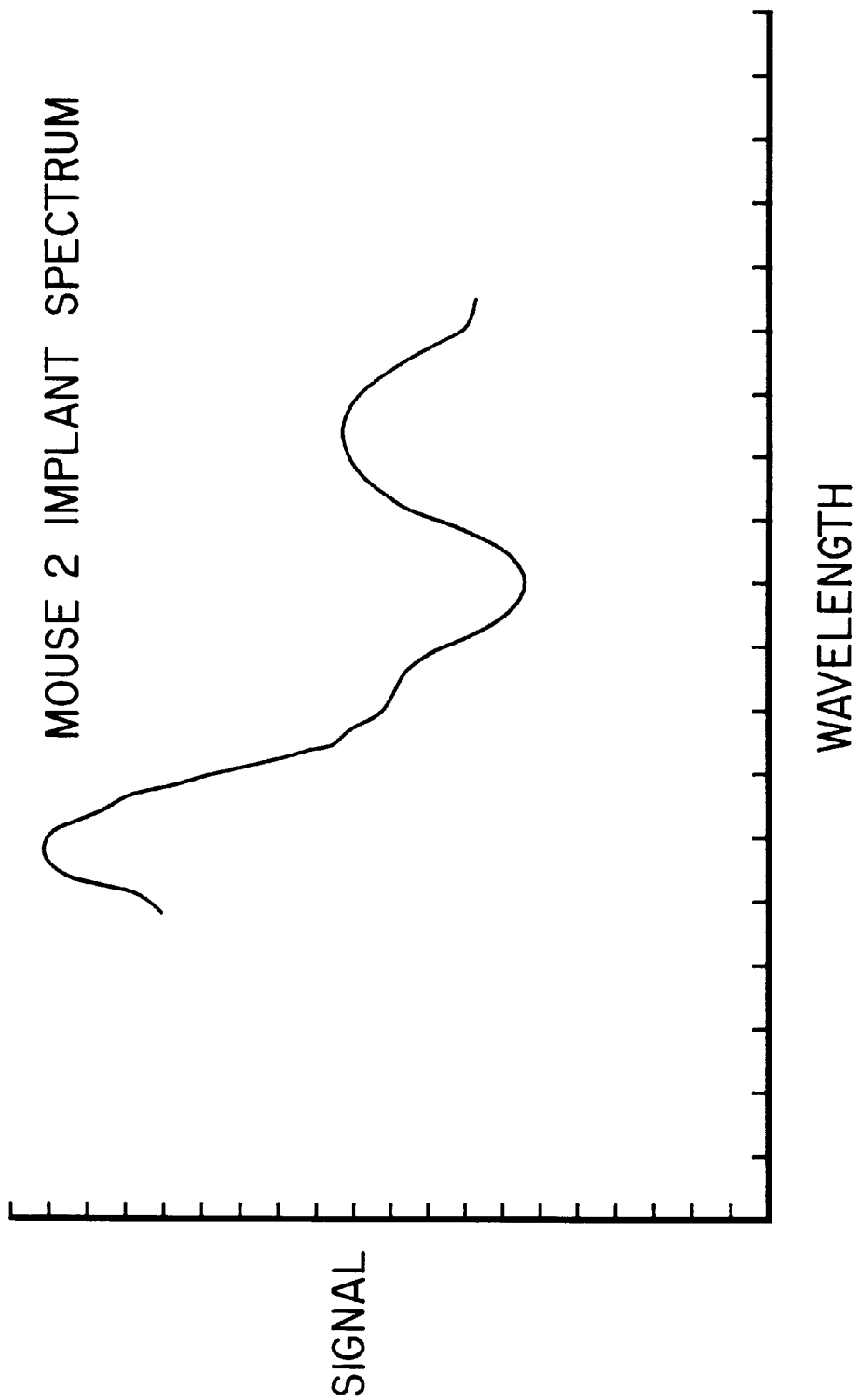

FIG. 10 is an emission spectrum for a sensor according to the invention implanted in a mouse.

Figure 11:

FIG. 11 is a photograph of a mouse provided with an implant for sensing glucose underneath the skin of its abdomen.

Figure 12A:
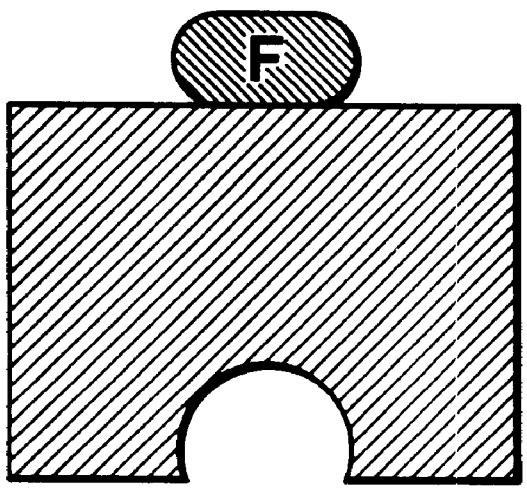

FIG. 12 is a schematic representation of a fluorescently labelled ligand binding to analyte.

Figure 13A:
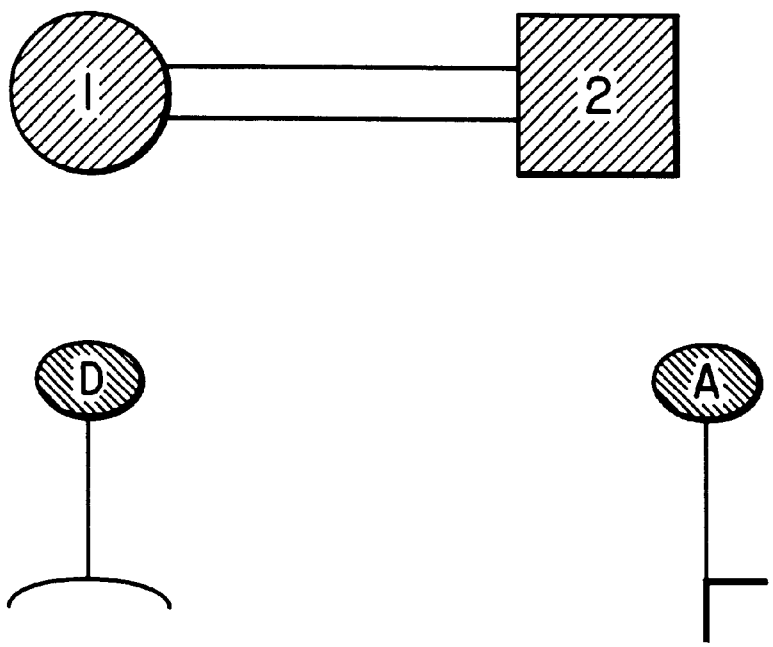
Figure 13B:
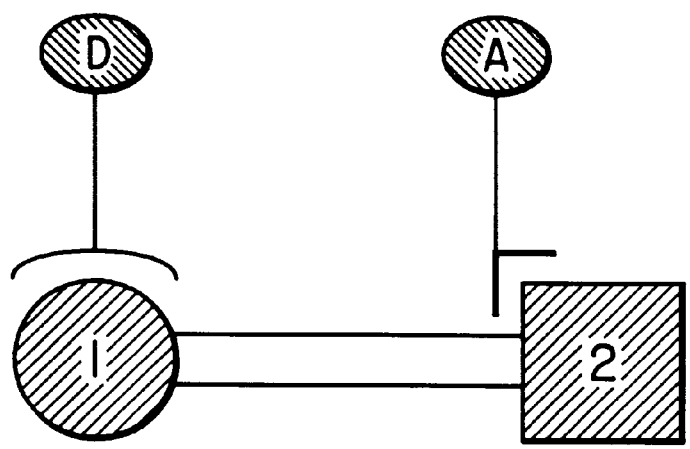

FIG. 13 is a schematic representation of fluorescently labelled donor and acceptor ligands which bind to different portions of an analyte.

DESCRIPTION OF THE PREFERRED EMBODIMENTS

A. Dual-Label Techniques

This group includes detection by means of FRET. We will first describe the basic elements of FRET.

Basic Elements of FRET

FRET generally involves the non-radiative transfer of energy between two fluorophores, one an energy donor (D) and the other an energy acceptor (A). Any appropriately selected donor-acceptor pair can be used, provided that the emission of the donor overlaps with the excitation spectra of the acceptor and both members can absorb light energy at one wavelength and emit light energy of a different wavelength.

The method is described below with particular reference to fluorescein and rhodamine as the donor-acceptor pair. As used herein, the term fluorescein refers to a class of compounds which includes a variety of related compounds and their derivatives. Similarly, as used herein, the term rhodamine refers to a class of compounds which includes a variety of related compounds and their derivatives. Other examples of donor/acceptor pairs are NBD N-(7-nitrobenz-2-oxa-1,3-diazol-4-yl) to rhodamine, NBD or fluorescein to eosin or erythrosin, dansyl to rhodamine, acridine orange to rhodamine.

Alternatively, both the donor and acceptor can absorb light energy, but only one of them emits light energy. For example, the donor can be fluorescent and the acceptor can be nonfluorescent, or vice versa. It is also possible to make use of a donor-acceptor pair in which the acceptor is not normally excited at the wavelength used to excite the (fluorescent) donor; however, nonradiative FRET causes acceptor excitation.

Although the donor and the acceptor are referred to herein as a "pair", the two "members" of the pair can, in fact, be the same substance. Generally, the two members will be different (e.g., fluorescein and rhodamine). It is possible for one molecule (e.g., fluorescein, rhodamine) to serve as both donor and acceptor; in this case, energy transfer is determined by measuring depolarization of fluorescence.

The concept of FRET is represented in FIGS. 1A and 1B. The absorbance and emission of donor, designated A(D) and E(D), respectively, and the absorbance and emission of acceptor, designated A(A) and E(A), respectively, are represented graphically in FIG. 1A. The area of overlap between the donor emission and the acceptor absorbance spectra (which is the overlap integral) is of importance. If excitation occurs at wavelength I, light will be emitted at wavelength II by the donor, but not at wavelength III by the acceptor because the acceptor does not absorb light at wavelength I.

The non-radiative transfer process which occurs is represented in FIG. 1B. D molecule absorbs the photon whose electric field vector is represented by E. The excited state of D is shown as a dipole with positive charge on one side and negative charge on the other. If an acceptor molecule (A) is sufficiently close to D (e.g., typically less than 100 Angstroms), an oppositely charged dipole is induced on it (it is raised to an excited state). This dipole-induced dipole interaction falls off inversely as the sixth power of donor-acceptor intermolecular distance.

Classically, partial energy transfer can occur. However, this is not what occurs in FRET, which is an all or nothing quantum mechanical event. That is, a donor is not able to give part of its energy to an acceptor. All of the energy must be transferred and energy transfer can occur only if the energy levels (i.e., the spectra) overlap. When A leaves its excited state, the emitted light is rotated or depolarized with respect to the incident light. As a result, FRET manifests itself as a decrease in fluorescence intensity (i.e., decrease in donor emission) at II, an appearance of fluorescence intensity at III (i.e., an increase in sensitized emission) and a depolarization of the fluorescence relative to the incident light.

A final manifestation of FRET is in the excited state lifetime. Fluorescence can be seen as an equilibrium process, in which the length of time a molecule remains in its excited state is a result of competition between the rate at which it is being driven into this state by the incident light and the sum of the rates driving it out of this state (fluorescence and non-radiative processes). If a further non-radiative process, FRET, is added (leaving all else unchanged), decay is favored, which means donor lifetime at II is shortened.

When two fluorophores whose excitation and emission spectra overlap are in sufficiently close proximity, the excited state energy of the donor molecule is transferred by a resonance dipole-induced dipole interaction to the neighboring acceptor fluorophore. In FRET, a sample or mixture is illuminated at a wavelength which excites the donor but not the acceptor molecule directly. The sample is then monitored at two wavelengths: that of donor emissions and that of acceptor emissions. If donor and acceptor are not in sufficiently close proximity, FRET does not occur and emissions occur only at the donor wavelength. If donor and acceptor are in sufficiently close proximity, FRET occurs. The results of this interaction are a decrease in donor lifetime, a quenching of donor fluorescence, an enhancement of acceptor fluorescence intensity, and depolarization of fluorescence intensity. The efficiency of energy transfer, $E_t$, falls off rapidly as the distance between donor and acceptor molecule, R, increases. For an isolated donor acceptor pair, the efficiency of energy transfer is expressed as:

$$E_t = 1/[1+(R/R_o)^6] \qquad (1)$$

where R is the separation distance between donor and acceptor and $R_o$ is the distance for half transfer. $R_o$ is a value that depends upon the overlap integral of the donor emission spectrum and the acceptor excitation spectrum, the index of refraction, the quantum yield of the donor, and the orientation of the donor emission and the acceptor absorbance moments. Forster, T., *Z Naturforsch.* 4A, 321–327 (1949); Forster, T., *Disc. Faraday So.* 27, 7–17 (1959).

Because of its $1/R^6$ dependence, FRET is extremely dependent on molecular distances and has been dubbed "the spectroscopic ruler". (Stryer, L., and Haugland, R. P., *Proc. Natl. Acad. Sci. USA*, 98:719 (1967). For example, the technique has been useful in determining the distances between donors and acceptors for both intrinsic and extrinsic fluorophores in a variety of polymers including proteins and nucleic acids. Cardullo et al. demonstrated that the hybridization of two oligodeoxynucleotides could be monitored using FRET (Cardullo, R., et al., *Proc. Natl. Acad. Sci.*, 85:8790–8794 (1988)).

Concept of Using FRET for Analyte Detection

In general, FRET is used for analyte detection is one of two ways. The first is a competitive assay in which an analogue to the analyte being detected and a ligand capable of binding to both analogue and analyte are labelled, one with a donor fluorophore and the other with an acceptor fluorophore. Thus, the analogue may be labelled with donor and the ligand with acceptor, or the analogue may be labelled with acceptor and the ligand with donor. When the labelled reagents contact analyte, analyte displaces analogue bound to ligand. Because ligand and analogue are no longer close enough to each other for FRET to occur, the fluorescence signal due to FRET decreases; the decrease correlates with the concentration of analyte (the correlation can be established in a prior calibration step).

In order to be able to reuse the fluorescence reagents, the binding between analyte and ligand should be reversible under physiological conditions. Similarly, the equilibrium binding constants associated with analyte-ligand binding and analogue-ligand binding should be such that analyte can displace analogue. In other words, analogue-ligand binding should not be so strong that analyte cannot displace analogue.

This approach is applicable to detection of carbohydrates, steroids, proteins, peptides, antigens, haptens, drugs, pesticides, theophylline, creatinine, and small organic molecules generally. In the case of carbohydrates such as glucose and fructose, suitable analogue-ligand combinations satisfying the above-described selection criteria include the following combinations: glycoconjugate-lectin, antibody-antigen, receptor-ligand, and enzyme-substrate. For example, in the case of glucose the combination of bovine serum albumin covalently labelled with glucose or glucose analogue (as the glycoconjugate) and Concanavalin A (as the lectin) have been found to be effective. To determine suitable combinations for other sugars, one can select a lectin that binds to the sugar and then use that lectin in combination with bovine serum albumin covalently labelled with that sugar or an analogous sugar.

In the case of analytes such as steroids, proteins, and peptides, the appropriate combination would be an analogue to the steroid, protein, or peptide, and an antibody (or antigen, where the protein or peptide is an antibody) or a receptor for the steroid, protein, or peptide. For example, in the case of steroids we refer to Haugland, R. P. (1989) Molecular Probes: Handbook of Fluorescent Probes and Research Chemicals, Molecular Probes, Eugene, Oreg. for preparation of suitable analogues. Using cholesterol as a representative example, derivatives can be prepared either by covalent attachment of a fluorophore (e.g., NBD or pyrene) to the aliphatic side chain or to a hydroxyl group (e.g., using anthracene as the fluorophore). For cholesterol, the molecules thus produced are, respectively, 22-(N-(7-nitrobenz-2-oxa-1,3diazol-4-yl) amino-23,24-bisnor-5-cholen-3B-ol; 1-pyrenemethyl 3B-hydroxy-22,23-bisnor-5-cholenate; and cholesteryl anthracene-9-carboxylate. The steroid can also be conjugated to a carrier protein or other macromolecule which would also be fluorescently tagged with donor or acceptor. The conjugation would again proceed via either the aliphatic side chain or the hydroxyl group.

Similar considerations apply in the case of glycoproteins, glycopeptides, and glycolipids. In the case of glycosylated hemoglobin, FRET between a labelled lectin and the heme itself could be measured (this would manifest itself as a quenching of fluorescence).

The second approach using FRET is to select two ligands that bind to different portions (sites) of the analyte molecule; in addition to being spatially different, the portions may be chemically different as well. This approach (illustrated schematically in FIG. 13) is applicable to detection of antigens, haptens, steroids, proteins, peptides, drugs, pesticides, theophylline, creatinine, and large organic molecules generally. The ligands could be two antibodies, two cell receptors, or an antibody and a cell receptor. For example, in the case of hormones such as HCG, FSH, and LSH the labelled ligands could be antibodies or cell receptors that bind to different portions of the hormone molecule.

One variation of this second approach is to detect antibodies such as anti-DNA antibodies in lupus patients by encapsulating two fluorescent DNA fragments, one labelled with donor and the other with acceptor, and then measuring FRET (which would occur if the antibody of interest were present and crosslinked the labelled fragments).

Another variation involves labelled oligonucleotide probes. As described in Cardullo, R., et al., *Proc. Natl. Acad. Sci.*, 85:8790–8794 (1988), the hybridization of two oligodeoxynucleotides can be monitored using FRET in conjunction with such probes. In this way, specific DNA sequences can be determined.

To assay overall DNA levels, reagents that bind non-specifically to DNA or RNA are used. Examples of such reagents include fluorescent intercalating dyes which show dramatic spectral shifts upon binding.

In yet another variation, a single material is labelled with both donor and acceptor fluorophores. The fluorescence change associated with the conformational change in the material upon binding to analyte is used as an indication of analyte presence. For example, the analyte may be a helical DNA molecule and the fluorescence reagent is a material labelled with donor and acceptor fluorophores that binds to the DNA. Binding changes the separation distance between the donor and acceptor, and thus the signal detected by FRET.

We now describe the use of FRET in a competitive binding assay format to determine glucose concentration.

Concept of Using FRET to Measure Glucose Concentrations

Figure 2:
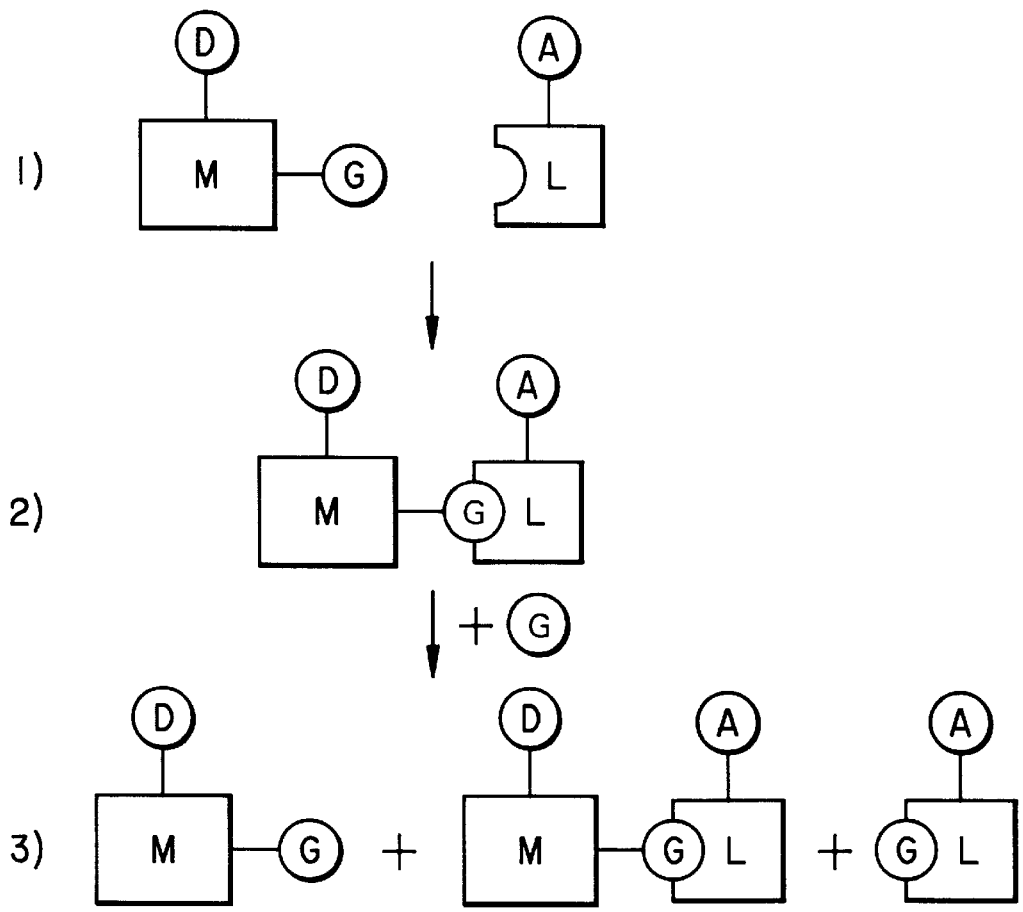
FIG. 2 is a graphic representation of the use of FRET to measure glucose concentrations in a sample.

The concept of using FRET to measure glucose concentrations in solution is represented in FIG. 2. One macromolecule (designated M) includes a number of covalently-bound fluorophores and glucose residues and is referred to as a glycoconjugate. A second macromolecule (designated L), e.g., lectin, includes a ligand which has a high degree of specificity for glucose (designated G) (e.g., concanavalin A) and a fluorophore which is generally not the same fluorophore as that on the first macromolecule.

One of these fluorophores is chosen to be a donor (designated D) and the other is an acceptor (designated A) as described previously. For the purposes of this illustration, the donor molecule has been placed on the glycoconjugate and the acceptor has been placed on the ligand. The association can then be diagrammed as:

DMG+AL→DMG-LA, where DMG stands for Donor-Macromolecule-Glucose, AL stands for Acceptor-Ligand, and DMG-LA represents the association between the glucose present in the first complex and the ligand present in the second complex. Upon association, the two macromolecules are now close enough to allow energy transfer between the donor and the acceptor to occur.

The presence of free glucose introduces a competitive inhibitor into the formula because free glucose competes with the conjugated glucose for the ligand. Thus, increasing concentrations of glucose produces a decrease in the amount of ligand binding to the glycoconjugate. At relatively low concentrations of glucose, the transfer efficiency will remain high, since little of the macromolecular association will be affected. At high concentrations of glucose, the transfer efficiency will be low, due to the fact that the glucose has successfully competed the ligand off of the complementary macromolecule. Referring to FIG. 2, at 1) no energy transfer occurs, at 2) complete energy transfer occurs, and at 3) partial energy transfer due to glucose competition occurs.

As described in the following sections, it has been shown that it is possible to obtain a reliable, repeatable measure of glucose in a sample containing glucose concentrations within the range typically found in normal individuals and in those in whom glucose homeostasis is altered (e.g., in diabetic and hypoglycemic patients). Further, it has been shown that the reactants used (i.e., fluorescently-labelled ligand and glycoconjugate) are stable and can be reused.

Competition experiments in which FRET was measured for various concentrations of glucose in Hanks Buffered Salt Solution (HBSS) were conducted. These experiments are described in detail in Example 3. Spectra were collected by exciting fluorescein at 472 nm and scanning the emission from 500–650 nm. Typically, fluorescence intensities were monitored at the emission maxima for fluorescein (about 520 nm) and rhodamine (about 600 nm). The measure of energy transfer in these studies was either the ratio of fluorescence intensities at 520 nm and 600 nm (i.e., FI 520/FI 600) as a function of glucose concentration or the quenching of fluorescein at 520 nm.

Figure 3:
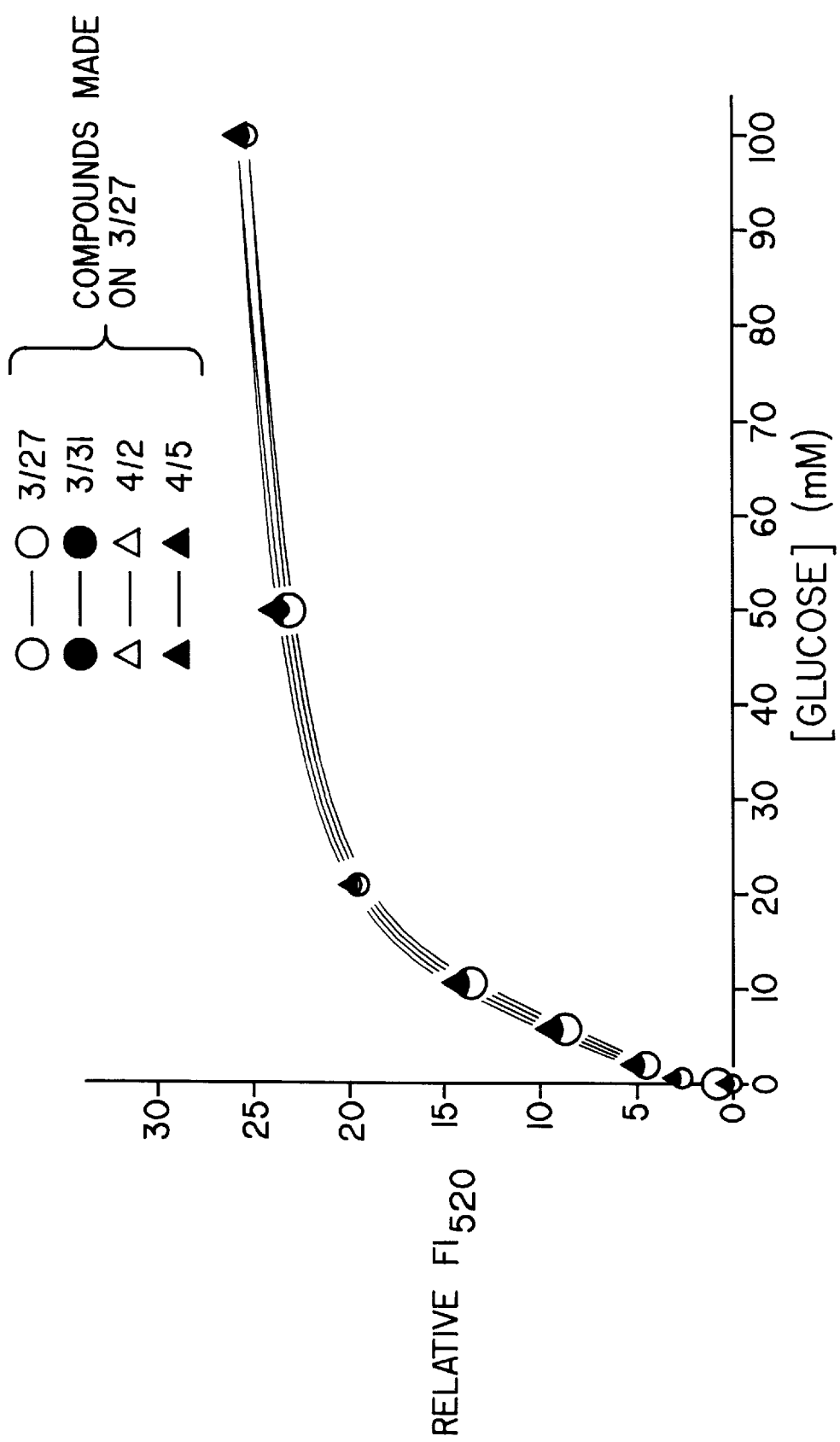
FIG. 3 is a graph representing the effect that increasing concentrations of glucose have on FRET between the fluorescently labelled ligand, Rhodamine-ConA (RC) and the fluorescently labelled glycoconjugate, fluorescein BSA-Glucose (FBG).

A number of observations were made during these trials that indicate that the method of the subject invention provides a reliable means of detecting glucose over a wide range (i.e., glucose concentrations found in normal, hypoglycemic and diabetic subjects). Firstly, the compounds were found to be stable. FIG. 3 shows that the compounds exhibited the same fluorescence properties over a one week time period in response to glucose concentration. Data in the graph reflect the change in fluorescence intensity at 520 nm from 0 mM glucose as a function of glucose concentration.

Another experiment testing the stability of the sensor is described in Example 4. In this experiment, titration curves were periodically prepared over the course of ten weeks for human serum samples containing various known concentrations of glucose. FIG. 8 demonstrates that the system continues to respond to glucose for 10 weeks. The data in the graph reflect the ratio of fluorescein emission (at 520 nm) to rhodamine emission (at 600 nm).

Figure 4:
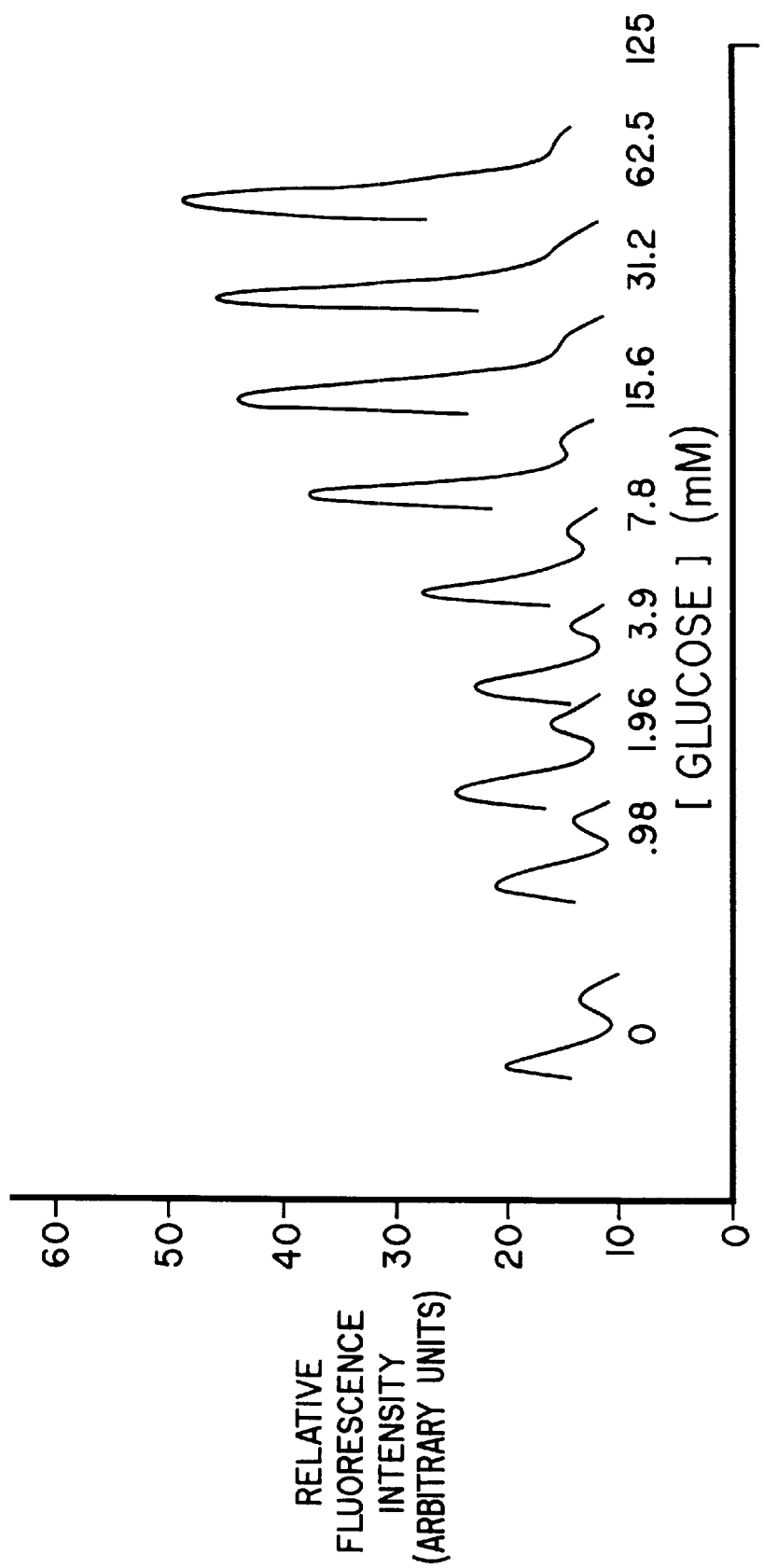
FIG. 4 is a graph representing FRET between FBG and RC dialyzed against various concentrations of glucose in Hanks Buffered Salt Solution (HBSS).

FIG. 4 shows that the FRET method was able to predict glucose concentrations accurately at concentrations up to 31 mM glucose (~600 mg/dL), which is well within and in excess of the desired range. Normal glucose concentrations in blood are usually between 80 and 120 mg/dL and diabetic levels can exceed 500 mg/dL. In the range of 0 to 31 mM glucose, the response by FRET was nearly linear with a coefficient of determination ($r^2$) of 0.983. Therefore, the sensor is reliable for detecting glucose concentrations over the entire physiological range (i.e., for normal and hyperglycemic (diabetic) individuals).

Figure 5:
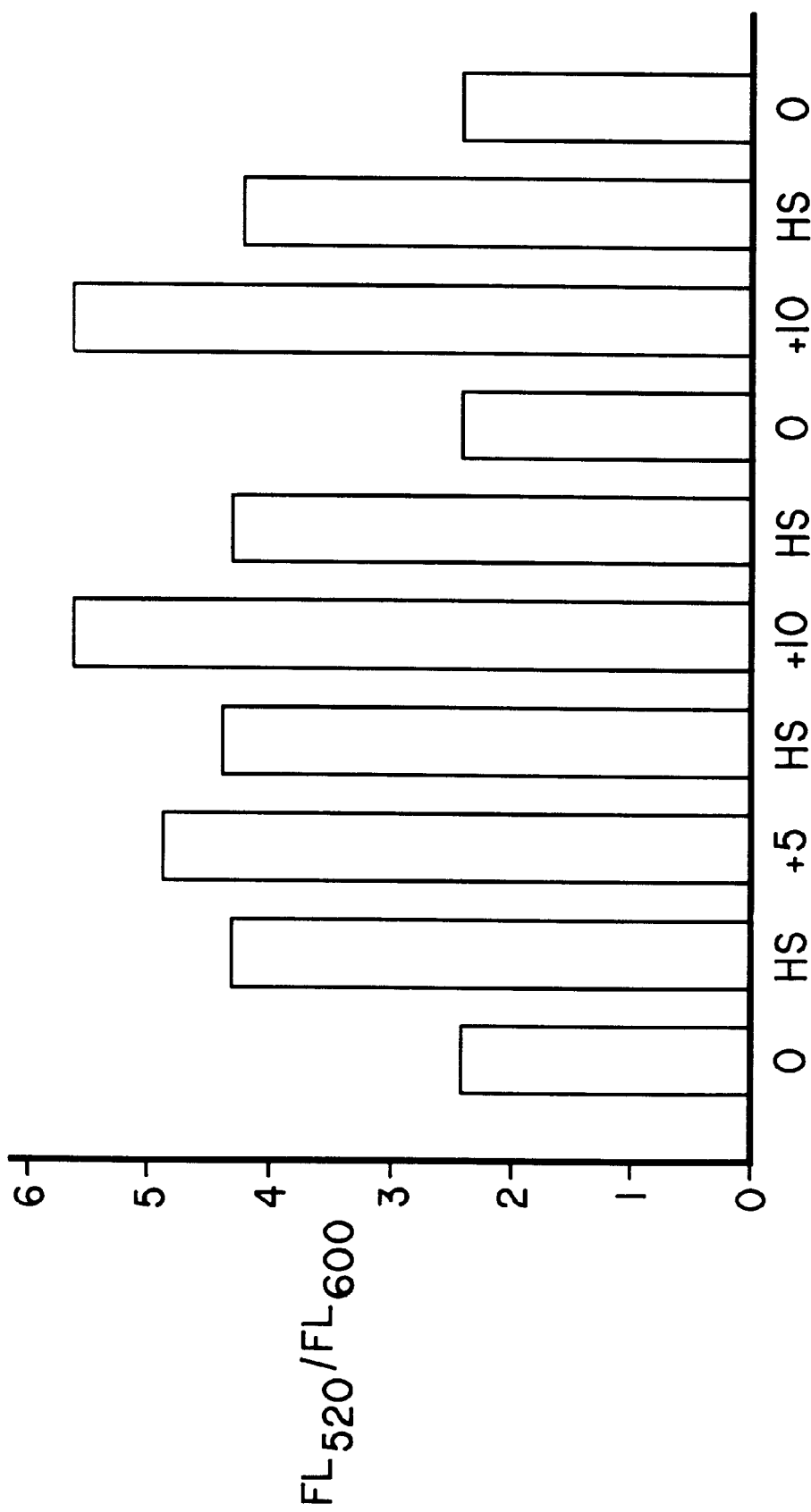
FIG. 5 is a bar graph of $Fl_{520}/Fl_{600}$ ratio for a sample of FBG and RC dialyzed sequentially against various different glucose concentrations in the following: (reading left to right on the X axis) (0) Hanks Buffered Salt Solution; (HS) normal horse serum; (+5) horse serum +5 mM glucose; (HS)

The components of the present invention were also found to be reusable. When FBG and RC were placed into 8–11 kD cutoff dialysis tubing and dialyzed against different glucose concentrations in serum, FRET accurately determined these concentrations in accordance with solution studies. The initial volume of FBG and RC in HBSS was 2 ml and dialyzed against different glucose concentrations in 50 ml volumes. In general, it took approximately 30 minutes to reach a plateau level in the $FI_{520}/FI_{600}$ ratio. As shown in FIG. 5, the response is reversible as the dialysis tubing was placed into different glucose concentrations and then equilibrated. Experiments in horse serum showed that the response was not affected by dialyzed components, but did shift the baseline due to light scattering.

Another experiment demonstrating reusability is described in Example 5. The results, shown in FIG. 9, demonstrated that the sensor could be used repeatedly to measure samples having various glucose concentrations without significant changes in the response.

The ability of the present method to determine the glucose concentration in hyperglycemic blood (i.e., a sample of normal blood augmented with glucose to produce glucose levels observed in diabetic individuals) was also assessed. FIGS. 6A and 6B shows the raw data scans from this experiment. The first (FIG. 6A) is an emission scan from 500 nm of a sample excited at 472 nm which does not contain glucose. It shows considerable energy transfer, as evidenced by the ratio of the two emission peaks. The rhodamine (second) peak is actually higher than the fluorescein (first) peak.

The second scan depicted in FIG. 6B shows the effect of dialyzing against a blood sample with hyperglycemic levels of glucose, here 317 mg/dL. The energy transfer decreases as seen both in the increase of the fluorescein emission peak and a concurrent decrease in the sensitized rhodamine emission.

The present method was shown to be effective in assessing glucose levels in blood and is sensitive in the hyperglycemic range in the following way: 150 μm of a mixture of Rh-Con A and FBG was microdialyzed for 15 minutes against 1500 μl samples of hyperglycemic blood. FIG. 7 shows that the initial fluorescein/rhodamine fluorescence ratio was just above 1.6 and that the fluorescein/rhodamine fluorescence ratio increased as a function of glucose concentration, saturating at about 40 mM glucose.

EXAMPLE 1

Preparation of FBG and RC

Fluorescein-BSA-Glucose (FBG) purchased from Sigma and Rhodamine-ConA (RC) purchased from Molecular Probes were dissolved in Hanks Buffered Salt Solution (HBSS) from Gibco to a final concentration of 2 mg/ml. The solutions were then centrifuged at 10,000 g for 30 min. to remove large particulates. The supernatant was then collected and placed on a 10,000 MW Amicon ultrafiltration device and centrifuged at 2,000 g until the ultra-filtrate had passed through the membrane. The retained material was then resuspended in 2 mls. of HBSS and this procedure was repeated until no free fluorescein or rhodamine was detected in the ultrafiltrate.

The final retained material was collected and resuspended in 2 ml. of HBSS and spun one more time at 10,000 g for 30 min. The supernatant was collected and stored at 4° C. until used for energy transfer experiments.

EXAMPLE 2
Determination of the Optimal Concentrations of Fluorescein-BSA Glucose and Rhodamine-ConA Before competition experiments could be performed with mannose and glucose, optimal concentrations of Fluorescein-BSA-Glucose (FBG) and Rhodamine-Con A (RC) had to be determined. In any solution study using energy transfer, one must avoid the trivial possibility that FRET is occurring simply because the molecules are close enough to one another in solution. Thus, FRET solution studies should ideally be done at concentrations less than 1 mM because at that concentration the molecules are separated by 120A units (far enough apart so they specifically interact).

Conversely, in these experiments, the concentrations of fluorophore must be high enough to be detected and the concentration of the two species (FBG and RC) must be above their binding constants ($K_D$s).

Initial concentrations of FBG and RC were approximately 2 mg/ml. Maximum transfer occurred when final concentration of FBG was approximately 2 $\mu$g/ml and the final concentration of RC was approximately 150 $\mu$g/ml. Optimization of FRET was determined by quenching of fluorescein fluorescence, which was 50% maximal at 30 $\mu$g/ml.

EXAMPLE 3
Competition Experiments with Mannose and Glucose

The spectrofluorimeter used for these studies was a Perkin-Elmer MPF-2 equipped with a temperature stage and interfaced to an Apple IIE computer.

Concanavalin A, (Con A) is a lectin that specifically binds glucose. A serial dilution of glucose was performed using approximately 2 $\mu$g/ml FBG and approximately 150 $\mu$g/ml RC from 0–5 mM glucose in HBSS. Various concentrations of glucose were the concentration of glucose increases, the fluorescence intensity at 520 nm increases, and that the ½ maximal response for glucose was approximately 1.87 mg/ml.

EXAMPLE 4
Titration Curve Stability Studies

Because the issue of reusability is related to the issue of stability, an experiment was carried out to demonstrate the chemical stability of the sensor. A sterile mixture of FBG (0.6 $\mu$M) and RC (4.6 $\mu$M) in Hepes Saline was prepared. From this mixture, 75 $\mu$L aliquots were prepared and stored in the dark at room temperature for up to eight weeks. Periodically, a set of aliquots was taken to prepare a titration curve using human serum samples (each representing a pool of donors) to which various known concentrations of glucose had been added. The curve was prepared by adding an aliquot of the FBG/RC solution to each serum/glucose sample and then measuring the F/R ratio for each sample. The results, graphically in FIG. 8, demonstrate that the sensor continues to respond to glucose for 10 weeks.

EXAMPLE 5
Reusability Study

The following experiment was performed to demonstrate that the same aliquot of RC-FBG mixture could be used over and over again to measure glucose concentration in various samples.

A mixture of RC (2 $\mu$M) and FBG (1 $\mu$M) in Hepes Saline was prepared. Approximately 30 $\mu$L of the mixture was placed in a polyacrylonitrile ("PAN-69") hollow fiber (inner diameter approx. 0.5 mm; length approx. 1 in.; molecular weight cutoff 10 kDa). PAN fibers were chosen because they are reasonably biocompatible and resist clogging. The ends of the fiber were sealed and an initial reading of the F/R ratio taken. The fiber was then sequentially equilibrated by dialysis for 10 minutes at room temperature against 200 $\mu$L samples of pooled human serum to which various known concentrations of glucose (measured using a Beckman glucose analyzer) had been added, after which the F/R ratio of each sample was measured. The fiber was then stored at 4° C. in human serum (55.6 mg/dL glucose) overnight and the samples re-measured 24 hours later. The data from both sets of readings is shown graphically in FIG. 9. The results from both days are essentially the same. Similar data (not shown) was obtained when measurements were taken on a third day. In addition, similar results were obtained using polysulfone fibers.

The results of this experiment demonstrate that the sensor can be used repeatedly to measure samples having various glucose concentrations without significant changes in the response.

B. Single Label Techniques

These techniques generally fall into two categories: (1) those involving direct binding of a fluorophore or compound labelled with the fluorophore to the analyte of interest, and (2) those involving a competitive assay in which the analyte and an analogue thereof compete for the same ligand (either the analogue or ligand being labelled with a fluorophore. Regardless of the category, however, fluorescence changes caused by the presence of analyte are detected by measuring changes in fluorescence intensity or in excitation or emission spectra, as described in the Summary of the Invention, above.

Figure 12B:
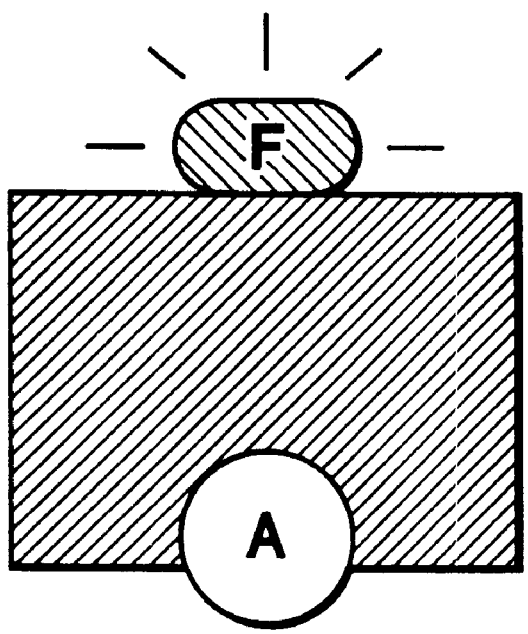

One embodiment of the single label technique is illustrated schematically in FIG. 12, in which a ligand labeled with a fluorescent group (designated F) binds to an analyte (designated A) causing a change in the fluorescence of the ligand as shown in FIG. 12B. In the case of a competitive assay protocol, an analogue capable of binding competitively to the ligand would also be included. An analyte having two binding sites designated 1 and 2, is shown in FIG. 13. When a ligand for site 1 labeled with a donor (designated D) and a ligand for site 2 labeled with an acceptor (designated A) concurrently bind to the analyte, the donor and acceptor are brought into proximity to each other and FRET occurs.

The direct binding protocol is particularly useful in the detection and measurement of ions. Examples include calcium, magnesium, sodium, chlorine, and potassium ions. Fluorescent probes for these ions (as well as other substances) are known and generally described, e.g., in Haugland, R.P. (1989) Molecular Probes: Handbook of Fluorescent Probes and Research Chemicals, Molecular Probes, Eugene, Oreg. The probes may be used alone or may be bonded to another compound, e.g., a macromolecule such as dextran. In fact, some of these probes are commercially available immobilized in a matrix or bound to macromolecules such as dextran.

Other examples include probes sensitive to blood pH (which involves detection of hydrogen ion concentration). Suitable pH probes are described in Haugland (above) and include SNARF, SNAFL, and BCECF.

In the case of calcium ions, many of the probes are derivatives of ethylene diamine tetraacetic acid (EDTA), a chelating agent that binds the calcium ion. They include, for example, the dyes Fura-2, Indo-1, quin-2, fluor-3, and rhod- 2, all of which are probes for calcium ions. In the case of quin-2, fluor-3, and rhod-2, fluorescence changes are measured by measuring changes in fluorescence intensity upon analyte binding. Fura-2 and Indo-1, on the other hand, undergo changes in excitation or emission spectra upon analyte binding.

The competitive binding approach is useful for the classes of analytes described above in the case of FRET detection. Selection of appropriate analogue-ligand combinations is as described therein, the only difference being that only one material (i.e., either analogue or ligand) is labelled with a fluorophore. Suitable fluorophores are those which are environmentally sensitive, i.e., probes whose fluorescence behavior changes depending on the chemical environment in which they find themselves (the presence of analyte being an example of an environmental change). Examples of suitable fluorophores include (in addition to those set out in the case of FRET) NBD, dansyl, pyrene, anthracene, and indocarbocyanine fluorophores.

C. Non-binding Technique

In this type of assay, the fluorescence reagent does not bind to the analyte (i.e., binding in and of itself does not cause the detectable fluorescence change).

One example of such a sensor includes an enzyme and a co-factor or substrate that reacts with the analyte in the presence of the enzyme, with an accompanying fluorescence change. For example, the sensor may be an ethanol sensor in which NAD (the co-factor) and alcohol dehydrogenase (the enzyme) are included in the sensor. In the presence of ethanol, NAD is converted to NADH, which is fluorescent. The change in fluorescence upon production of NADH is used to detect the presence and concentration of alcohol in the body.

Another example of such a sensor is a glucose sensor that proceeds by way of two reactions: an initial enzyme reaction that converts glucose into a detectable product and an indicator reaction that detects the product. In the first reaction, glucose reacts in the presence of a first enzyme (glucose oxidase) to produce hydrogen peroxide. In the second reaction, the presence of hydrogen peroxide is detected by a dye (leuco dye) in a reaction catalyzed by a second enzyme (peroxidase). The change in fluorescence upon production of hydrogen peroxide (as evidenced by the dye) indicates the presence and concentration of glucose. The sensor thus includes two enzymes (peroxidase and glucose oxidase) and a fluorophore (e.g., leuco dye) sensitive to the reaction product of the first reaction.

In another example of such a sensor, the analyte is an enzyme. The sensor includes a substrate that is cleaved by the enzyme to create by-products having different fluorescence properties compared to the uncleaved substrate. For example, the enzyme may be trypsin and the substrate may be N-CBZ-Gly-Gly-Arg-beta-naphthylamide HCL. Cleavage releases an N-CBZ-containing fragment whose fluorescence properties are different from the uncleaved substrate.

In another example of such a sensor, the sensor includes a co-factor or substrate that reacts with an enzyme to cause a detectable fluorescence change, and two ligands that bind to different portions of the analyte. Each ligand is labelled with a portion of the enzyme that reacts with the substrate or co-factor. The two enzyme portions are different from each other. Moreover, individually they are incapable of interacting with the substrate or co-factor to produce a detectable fluorescence change. However, when the two labelled ligands bind to analyte the individual enzyme portions interact with each other to reconstitute the enzyme (the enzyme portions are chosen such that reconstitution does not occur, or occurs only to a minimal extent, until ligand binding to analyte occurs). Once the enzyme is reconstituted, it can now react with the substrate or co-factor.

In a variation of this protocol, an analogue of the analyte is labelled with one portion of the enzyme and a ligand capable of binding to both analogue and analyte is labelled with the other portion. When analogue and ligand bind to each other, the enzyme is reconstituted and reaction with substrate or co-factor occurs. Once again, the enzyme portions are chosen such that reconstitution doe not occur, or occurs only to a minimal extent, until analogue-ligand binding occurs. The presence of analyte disrupts analogue-ligand binding, and thus enzyme reconstitution. As a result, fluorescence associated with reaction between enzyme and substrate or co-factor decreases, the decreases being associated with analyte presence and concentration. Because reaction with substrate or co-factor occurs in the absence of analyte, the substrate/co-factor and enzyme should be chosen such that this reaction occurs slowly. This will minimize depletion of substrate/co-factor, thereby enabling the sensor to be used over extended periods of time.

D. In Vivo Use

In vivo embodiments of this invention are directed to measurement of analytes by placing the fluorescence reagent in communication with (e.g., contacting) body fluid containing the analyte of interest. The reactants comprising the fluorescence reagent can be placed in, on, or under the skin. Alternatively, the reactants can be placed within an organ or a vessel (e.g., a vein or artery) in which they are in communication with the analyte, which can then be measured by the present method. In the embodiment in which the reactants are positioned in, on or under the skin, the analyte is detected by illuminating the skin transdermally. The fluorescence signal is then detected transdermally using, e.g., a fluorimeter.

A variety of modes of placing the reactants in communication with the analyte may be employed. The encapsulated sensor can be implanted anywhere in the body. The reactants can be introduced into the body in any type of supporting or surrounding material which retains the reactants at the desired location and also allows contact or communication with the analyte such that it can be measured (e.g., its concentration can be determined by the present method). The sensor could also be provided with a semipermeable membrane that allows analyte to diffuse freely into and out of the sensor, but not the fluorescence reagents. Selectivity can be based upon molecular size or upon electrostatic or chemical characteristics.

Some or all of the reactants comprising the fluorescence reagent may be immobilized, e.g., on a substrate or within the pores of a porous matrix. Such an approach would be particularly useful in the case of assays based upon a single reactant that interacts with the analyte and causes a quenching/enhancement of fluorescence or a change in emission or excitation spectrum. However, immobilization techniques can be used in the case of the multi-component competitive assay format as well. For example, in the case of a competitive assay involving a fluorescently labelled analogue and a ligand, the analogue could be immobilized on the substrate and the ligand attached to the analogue via a long, flexible, linker arm.

In another procedure, reactants may be mixed with an adjuvant, e.g., silicone or fluorocarbon oils, in which the reactants freely diffuse (as opposed to being immobilized) and interact with each other, and injected as a bolus intra- or subcutaneously. The adjuvant must exchange the analyte (but not the reactants) with the surrounding body fluid, must allow all the reactants to interact successfully, and must be immiscible (or only slowly miscible) with water. This approach is particularly useful in FRET-based assays because it allows the labelled reactants to freely diffuse and associate or dissociate with each other.

The reactants may be tattooed onto the skin. For example, the reactants may be tattooed directly or admixed with an adjuvant and then tattooed. They may also be encapsulated in microcapsules and the microcapsules then tattooed onto the skin.

In another embodiment, the reagents may be contained in a transcutaneous patch.

The reactants may also be modified in such a way that when injected subcutaneously, they become bound to cell structure and therefore remain fixed in situ under the skin. For example, RC is known to bind to cells. In addition, the albumin of the FBG complex can be engineered to include a reactive group that binds cells.

In order to determine whether, as an example, an in vivo glucometer is feasible, experiments were conducted in which solutions of RC (150 μg/ml) and FBG (2 μg/ml) were injected into mouse skin. Illumination with a laser at the appropriate wavelengths produced strong signals from both the fluorescein and the rhodamine; energy transfer occurred and was detected.

Any in vivo mode of placing the reactants in communication with analyte can be modified to include a drug delivery system. The drug delivery system therefore inject drug into a patient upon detection of inappropriately high analyte levels. One example would be an insulin pump that injected insulin upon detection of abnormally high glucose levels. Another would be a pump that injected chemotherapeutic agent.

To demonstrate that a sensor according to the invention will work in vivo, the following experiment was performed. Although described here for glucose, it is readily applicable to other analytes as well.

EXAMPLE 6

A Pan-69 fiber (approx. 0.75 inches long) was loaded with RC (9 μM) and FBG (0.4 μM) as described above in Example 5. The fur covering the abdomen of a diabetic mouse was removed using a depilatory and the fiber surgically implanted subcutaneously under the denuded skin. The mouse was positioned in a fluorimeter so that approximately 0.5 inch of the implanted fiber was illuminated by a focused xenon lamp (472 nm) at what is normally the center of the cuvette. Slits for both monochromators were set at 8 nm. The emission signal was scanned from 500 nm. The results are shown in FIG. 10.

This experiment demonstrates that the sensor can be implanted and provide a detectable signal which enables one to determine the 520/600 ratio as a measure of energy transfer.

FIG. 11 is a photograph prepared from a low light video of a mouse provided with an implant underneath the skin of its abdomen as described above. The mouse is lying on a microscope stage which is used as a convenient light source. The implant is excited with green light. The emitted red light is observed through a red filter. The glowing line on the mouse's abdomen is the fluorescence from the implant.

Other embodiments are within the following claims.

What is claimed is:

1. An in vivo method for determining an analyte in the body fluids of an individual comprising the steps of
    a) placing a sensor in communication with the body fluids of said individual suspected of containing said analyte in such a way that once in place said sensor does not exit the skin of the individual,
        said sensor comprising a fluorescence reagent for detecting said analyte that reversibly binds to said analyte,
        said fluorescence reagent having a fluorescence intensity, an emission spectrum, an excitation spectrum, or an excited state lifetime in the presence of said analyte that is different from its fluorescence intensity, emission spectrum, excitation spectrum, or excited state lifetime in the absence of said analyte,
        said sensor being configured to retain said fluorescence reagent while allowing said analyte to diffuse into and out of said sensor;
    b) transdermally illuminating said sensor; and
    c) measuring the fluorescence intensity, emission spectrum, excitation spectrum, or excited state lifetime of said fluorescence reagent relative to the fluorescence intensity, emission spectrum, excitation spectrum, or excited state lifetime of said fluorescence reagent in the absence of said analyte; and
    d) correlating the change in fluorescence intensity, emission spectrum, excitation spectrum, or excited state lifetime of said fluorescence reagent with the presence or amount of said analyte in said individual.

2. The method of claim 1 wherein said analyte is a carbohydrate.

3. The method of claim 2 wherein said carbohydrate is glucose or a derivative thereof.

4. The method of claim 1 wherein said fluorescence reagent comprises a fluorophore or compound labelled with said fluorophore that binds directly to said analyte.

5. The method of claim 4 wherein said fluorophore or compound labelled with said fluorophore exhibits a change in fluorescence intensity upon binding to said analyte, and said fluorescence is measured by measuring said change in fluorescence intensity.

6. The method of claim 4 wherein said fluorophore or compound labelled with said fluorophore exhibits a change in excitation or emission spectrum upon binding to said analyte, and said fluorescence is measured by measuring said change in the excitation or emission spectrum.

7. The method of claim 6 wherein the change in said excitation or emission spectrum of said fluorophore or compound labelled with said fluorophore is measured by measuring (a) the appearance or disappearance of emission peaks, (b) the ratio of the signal observed at two or more emission wavelengths, (c) the appearance or disappearance of excitation peaks, or (d) the ratio of the signal observed at two or more excitation wavelengths.

8. The method of claim 4 wherein said fluorophore or compound labelled with said fluorophore exhibits a change in excited state lifetime upon binding to said analyte, and said fluorescence is measured by measuring said change in the excited state lifetime.

9. The method of claim 1 wherein said fluorescence reagent comprises an analogue of said analyte labelled with a flourophore and a ligand capable of binding to both said analogue and said analyte.

10. The method of claim 9 wherein said analogue labelled with said fluorophore exhibits a change in fluorescence intensity upon binding to said analyte, and said fluorescence is measured by measuring said change in fluorescence intensity.

11. The method of claim 9 wherein said analogue labelled with said fluorophore exhibits a change in excitation or emission spectrum upon binding to said analyte, and said fluorescence is measured by measuring said change in the excitation or emission spectrum.

12. The method of claim 11 wherein the change in said excitation or emission spectrum of said analogue labelled with said fluorophore is measured by measuring (a) the appearance or disappearance of emission peaks, (b) the ratio of the signal observed at two or more emission wavelengths, (c) the appearance or disappearance of excitation peaks, or (d) the ratio of the signal observed at two or more excitation wavelengths.

13. The method of claim 9 wherein said analogue labelled with said fluorophore exhibits a change in excited state lifetime upon binding to said analyte, and said fluorescence is measured by measuring said change in the excited state lifetime.

14. The method of claim 1 wherein said fluorescence reagent comprises an analogue of said analyte and a ligand labelled with a fluorophore and capable of binding to both said analogue and said analyte.

15. The method of claim 14 wherein said ligand labelled with said fluorophore exhibits a change in fluorescence intensity upon binding to said analyte, and said fluorescence is measured by measuring said change in fluorescence intensity.

16. The method of claim 14 wherein said ligand labelled with said fluorophore exhibits a change in excitation or emission spectrum upon binding to said analyte, and said fluorescence is measured by measuring said change in the excitation or emission spectrum.

17. The method of claim 16 wherein the change in said excitation or emission spectrum of said ligand labelled with said fluorophore is measured by measuring (a) the appearance or disappearance of emission peaks, (b) the ratio of the signal observed at two or more emission wavelengths, (c) the appearance or disappearance of excitation peaks, or (d) the ratio of the signal observed at two or more excitation wavelengths.

18. The method of claim 14 wherein said ligand labelled with said fluorophore exhibits a change in excited state lifetime upon binding to said analyte, and said fluorescence is measured by measuring said change in the excited state lifetime.

19. The method of claim 1 wherein said fluorescence reagent is labelled with an energy-absorbing donor molecule and an energy-absorbing acceptor molecule, the excited state energy level of the donor overlapping with the excited state energy level of the acceptor, and said fluorescence is measured by determining the extent to which non-radiative fluorescence resonance energy transfer occurs between the donor and the acceptor upon binding.

20. The method of claim 19 wherein said fluorescence reagent comprises a specific binding pair, one member of which is labelled with said donor molecule and the other member of which is labelled with said acceptor molecule.

21. The method of claim 20 wherein said specific binding pair comprises a ligand capable of binding to said analyte and an analogue of said analyte capable of binding to said ligand.

22. The method of claim 19 wherein said fluorescence reagent comprises (a) a first ligand labelled with said energy-absorbing donor molecule and capable of binding to a first portion of said analyte and (b) a second ligand labelled with said energy-absorbing acceptor molecule and capable of binding to a second portion of said analyte different from said first portion, and said fluorescence is measured by determining the extent to which non-radiative fluorescence resonance energy transfer occurs between the donor and the acceptor upon binding.

23. The method of claim 19 wherein said fluorescence reagent comprises an agent capable of binding to said analyte, said agent being labelled with both said energy-absorbing donor molecule and said energy-absorbing acceptor molecule, said fluorescence being measured by determining the extent to which non-radiative fluorescence resonance energy transfer occurs between the donor and the acceptor upon binding.

24. The method of claim 19 wherein said illumination excites the donor and non-radiative fluorescence resonance energy transfer is determined by measuring the ratio of the fluorescence signal at two emission wavelengths, one of which is due to donor emission and the other of which is due to acceptor emission.

25. The method of claim 19 wherein said illumination is chosen such that it excites the donor at a first wavelength and the acceptor at a second wavelength, and non-radiative fluorescence resonance energy transfer is determined by measuring the ratio of the fluorescence signal due to the acceptor following donor excitation and the fluorescence signal due to the acceptor following acceptor excitation.

26. The method of claim 19 wherein said non-radiative fluorescence resonance energy transfer is determined by assessing whether there is a decrease in donor lifetime, a quenching of donor fluorescence, or an enhancement of acceptor fluorescence intensity.

27. The method of claim 19 wherein one or both of the donor-acceptor pair are fluorophores.

28. An in vivo method for determining an analyte in the body fluids of an individual comprising the steps of
  a) placing a sensor in communication with the body fluids of said individual suspected of containing said analyte,
    said sensor comprising a fluorescence reagent for detecting said analyte that reversibly binds to said analyte,
    said sensor being configured to retain said fluorescence reagent while allowing analyte to diffuse into and out of said sensor,
    said fluorescence reagent comprising an energy-absorbing donor molecule and an energy-absorbing acceptor molecule, the excited state energy level of the donor overlapping with the excited state energy level of the acceptor;
  b) transdermally illuminating said sensor so as to
    i) excite the donor or
    ii) excite both the donor and acceptor; and
  c) measuring the fluorescence from said fluorescence reagent associated with the presence of said analyte in said individual by determining the extent to which non-radiative fluorescence resonance energy transfer occurs between the donor and the acceptor upon binding,
    said non-radiative fluorescence resonance energy transfer being determined by measuring
      i) the ratio of the fluorescence signal at two emission wavelengths, one of which is due to donor emission and the other of which is due to acceptor emission, when only the donor is excited,
      ii) the ratio of the fluorescence signal due to the acceptor following donor excitation and the fluorescence signal due to the acceptor following acceptor excitation,
      iii) a change in donor lifetime,
      iv) quenching of donor fluorescence, or
      v) an enhancement of acceptor fluorescence intensity; and
  d) correlating said non-radiative fluorescence resonance energy transfer with the presence or amount of said analyte in said individual.

29. An in vivo sensor for determining an analyte in the body fluids of an individual comprising a fluorescence reagent for determining said analyte that reversibly binds to said analyte,
  said fluorescence reagent having a fluorescence intensity, an emission spectrum, an excitation spectrum, or an excited state lifetime in the presence of said analyte that is different from its fluorescence intensity, emission spectrum, excitation spectrum, or excited state lifetime in the absence of said analyte, said sensor being configured such that (a) once implanted in the individual said sensor does not exit the skin of the individual, and (b) said fluorescence reagent is retained within said sensor while said analyte is allowed to diffuse into and out of said sensor.

30. An in vivo sensor for determining an analyte in the body fluids of an individual comprising a fluorescence reagent for determining said analyte that reversibly binds to said analyte, said fluorescence reagent comprising an energy-accepting donor molecule and an energy-absorbing acceptor molecule, the excited state energy level of the donor overlapping with the excited state energy level of the acceptor, said sensor being configured such that (a) once implanted in the individual said sensor does not exit the skin of the individual, and (b) said fluorescence reagent is retained within said sensor while said analyte is allowed to diffuse into and out of said sensor.

* * * * *